US011852707B2

(12) United States Patent
Zheng et al.

(10) Patent No.: US 11,852,707 B2
(45) Date of Patent: Dec. 26, 2023

(54) SYSTEMS AND METHODS FOR SIMULTANEOUS MULTI-SLICE MAGNETIC RESONANCE IMAGING

(71) Applicant: SHANGHAI UNITED IMAGING HEALTHCARE CO., LTD., Shanghai (CN)

(72) Inventors: Yuan Zheng, Houston, TX (US); Lele Zhao, Shanghai (CN); Jian Xu, Houston, TX (US); Weiguo Zhang, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 816 days.

(21) Appl. No.: 16/658,297

(22) Filed: Oct. 21, 2019

(65) Prior Publication Data

US 2021/0116527 A1  Apr. 22, 2021

(51) Int. Cl.
*G01R 33/483* (2006.01)
*A61B 5/055* (2006.01)
*G01R 33/561* (2006.01)

(52) U.S. Cl.
CPC .......... *G01R 33/4835* (2013.01); *A61B 5/055* (2013.01); *G01R 33/5616* (2013.01)

(58) Field of Classification Search
CPC ............ G01R 33/4835; G01R 33/5616; G01R 33/5614; G01R 33/5617; G01R 33/5611; G01R 33/4818; G01R 33/54; G01R 33/5608; A61B 5/055
See application file for complete search history.

(56) References Cited

U.S. PATENT DOCUMENTS

| 5,830,143 A | 11/1998 | Mistretta et al. |
| 5,910,728 A * | 6/1999 | Sodickson ......... G01R 33/5611 324/309 |
| 2003/0016016 A1 | 1/2003 | Fautz |

(Continued)

FOREIGN PATENT DOCUMENTS

EP  3432019 A1  1/2019

OTHER PUBLICATIONS

Barth M et al., Simultaneous Multislice (SMS) Imaging Techniques, Magnetic Resonance in Medicine, 75(1):63-81, 2016.

(Continued)

*Primary Examiner* — Joseph M Santos Rodriguez
*Assistant Examiner* — Amy Shafqat
(74) *Attorney, Agent, or Firm* — METIS IP LLC

(57) ABSTRACT

The present disclosure provides a system for SMS MRI. During each of a plurality of frames, the system may cause an MRI scanner to apply a plurality of PE steps to each of a plurality of slice locations of a subject to acquire echo signals. A phase modulation magnetic field gradient may be applied during each of at least some of the PE steps in the frame. For each frame, the system may reconstruct an aliasing image representative of the slice locations in the frame based on the corresponding echo signals. The system may also generate a plurality of reference slice images based on the aliasing images. The system may further reconstruct at least one slice image based on the aliasing images and the reference slice images. Each of the slice image may be representative of one of the slice locations in one of the frames.

17 Claims, 12 Drawing Sheets

(56) References Cited

U.S. PATENT DOCUMENTS

| | | | |
|---|---|---|---|
| 2004/0155652 | A1 | 8/2004 | Sodickson |
| 2008/0009705 | A1 | 1/2008 | Furudate |
| 2009/0179641 | A1 | 7/2009 | Matsuda et al. |
| 2011/0254548 | A1* | 10/2011 | Setsompop .......... G01R 33/543 324/309 |
| 2012/0319686 | A1* | 12/2012 | Jesmanowicz ... G01R 33/56545 324/309 |
| 2014/0111201 | A1* | 4/2014 | Kim ................... G01R 33/4835 324/309 |
| 2014/0225612 | A1 | 8/2014 | Polimeni et al. |
| 2015/0115955 | A1 | 4/2015 | Lee et al. |
| 2016/0341807 | A1 | 11/2016 | Bilgic et al. |
| 2017/0234954 | A1 | 8/2017 | Lee et al. |
| 2018/0372824 | A1 | 12/2018 | Saito et al. |
| 2019/0120922 | A1 | 4/2019 | Wheaton |
| 2019/0385309 | A1 | 12/2019 | Lyu et al. |
| 2020/0319283 | A1 | 10/2020 | Wang |

OTHER PUBLICATIONS

Setsompop K et al., Blipped-Controlled Aliasing in Parallel Imaging for Simultaneous Multislice Echo Planar Imaging with Reduced g-factor Penalty, Magnetic Resonance in Medicine, 67(5):1210-1224, 2012.

Breuer FA et al., Controlled Aliasing in Parallel Imaging Results in Higher Acceleration (CAIPIRINHA) for Multi-Slice Imaging, Magnetic Resonance in Medicine, 53(3):684-691, 2005.

Ferrazzi G et al., Autocalibrated Multiband CAIPIRINHA with Through-Time Encoding: Proof of Principle and Application to Cardiac Tissue Phase Mapping, Magnetic Resonance in Medicine, 81(2):1016-1030, 2019.

Yuan Zheng et al., Comparison of Methods for Simultaneous Multi-Slice Balanced SSFP Imaging, The International Society for Magnetic Resonance in Medicine 2017, 3833: 1-2, 2017.

Jingyuan Lyu et al., Toward single breath-hold whole-heart coverage compressed sensing MRI using VAriable spatial-temporal LAtin hypercube and echo-Sharing (VALAS), The International Society for Magnetic Resonance in Medicine 2019, 4752: 1-3, 2019.

John Pauly, Partial k-Space Reconstruction, Stanford University notes, 11-23, 2005.

Douglas C. Noll et al., Homodyne Detection in Magnetic Resonance Imaging, IEEE Transactions on Medical Imaging, 10(2): 154-163, 1991.

Scott B. Reeder et al., Homodyne Reconstruction and IDEAL Water-Fat Decomposition, Magnetic Resonance in Medicine, 54(3): 586-593, 2005.

R. Loudon, Quantum Noise in Homodyne Detection, Quantum Optics IV, 70-80, 1986.

Ronald Dean Chaney, Feature Extraction Without Edge Detection, Massachusetts Institute of Technology, 1993, 153 pages.

Huang, Xiaoqian et al., Accelerated Cardiac CINE Imaging with CAIPIRINHA and Partial Parallel Acquisition, Chinese Journal of Magnetic Resonance, 34(3): 283-293, 2017.

Sebastian Krohn et al., Multi-slice real-time MRI of temporomandibular joint dynamics, Dentomaxillofacial Radiology, 2018, 6 pages.

First Office Action in Chinese Application No. 202010663207.2 dated Nov. 3, 2022, 15 pages.

\* cited by examiner

600

---

During each of a plurality of frames, causing an MRI scanner to apply a plurality of PE steps to each of a plurality of slice locations of a subject to acquire a set of echo signals — 601

For each of the plurality of frames, reconstructing, based on the corresponding set of echo signals, an aliasing image representative of the plurality of slice locations in the frame — 602

Generating, based on the plurality of aliasing images, a plurality of reference slice images — 603

Reconstructing, based on the plurality of aliasing images and the plurality of reference slice images, at least one slice image — 604

FIG. 6

BSSFP 1100  
Frame 3

| | PE 1 | PE 2 | PE 3 | PE 4 | PE 5 | PE 6 | ... |
|---|---|---|---|---|---|---|---|
| Gz | | | | | | | |
| ADC | | | | | | | |
| S3 | 0 | 0 | 0 | 0 | 0 | 0 | |
| S4 | -2π/3 | 0 | 2π/3 | -2π/3 | 0 | 2π/3 | |
| S5 | -4π/3 | 0 | 4π/3 | -4π/3 | 0 | 4π/3 | |

BSSFP 1100  
Frame 4

| | | | | | | | ... |
|---|---|---|---|---|---|---|---|
| Gz | | | | | | | |
| ADC | | | | | | | |
| S3 | 0 | 0 | 0 | 0 | 0 | 0 | |
| S4 | 0 | 2π/3 | -2π/3 | 0 | 2π/3 | -2π/3 | |
| S5 | 0 | 4π/3 | -4π/3 | 0 | 4π/3 | -4π/3 | |

BSSFP 1100  
Frame 5

| | | | | | | | ... |
|---|---|---|---|---|---|---|---|
| Gz | | | | | | | |
| ADC | | | | | | | |
| S3 | 0 | 0 | 0 | 0 | 0 | 0 | |
| S4 | 2π/3 | -2π/3 | 0 | 2π/3 | -2π/3 | 0 | |
| S5 | 4π/3 | -4π/3 | 0 | 4π/3 | -4π/3 | 0 | |

FIG. 11

SYSTEMS AND METHODS FOR SIMULTANEOUS MULTI-SLICE MAGNETIC RESONANCE IMAGING

TECHNICAL FIELD

The present disclosure generally relates to magnetic resonance imaging (MRI), and more particularly, relates to systems and methods for simultaneous multi-slice (SMS) MRI.

BACKGROUND

SMS imaging has been used in MRI to allow an excitation of a plurality of slice locations of a subject (e.g., a patient) at the same time to accelerate the scanning process. Conventionally, an additional reference scan may need to be performed to acquire reference data of each of the slice locations for slice separation. For example, reference slice images of the slice locations may be reconstructed and coil sensitivity profiles of different receiver coils may be determined. A slice image of each individual slice location may be separated from an aliasing image acquired in SMS based on the coil sensitivity profiles. However, the additional reference scan may cause additional scan time and impair the benefit of SMS. Therefore, it is desirable to provide systems and methods for SMS MRI, thereby obviating the need for an additional reference scan and improving imaging efficiency.

SUMMARY

According to one aspect of the present disclosure, a system for SMS MRI is provided. The system may include at least one storage device including a set of instructions, and at least one processor configured to communicate with the at least one storage device. When executing the set of instructions, the at least one processor may be configured to direct the system to perform the following operations. During each of a plurality of frames, the at least one processor may be configured to direct the system to cause an MRI scanner to apply a plurality of phase-encoding (PE) steps to each of a plurality of slice locations of a subject to acquire a set of echo signals. A phase modulation magnetic field gradient may be applied during each of at least some of the plurality of PE steps in the frame. For each of the plurality of frames, the at least one processor may be configured to direct the system to reconstruct an aliasing image representative of the plurality of slice locations in the frame based on the corresponding set of echo signals. The at least one processor may also be configured to direct the system to generate a plurality of reference slice images based on the plurality of aliasing images. Each of the plurality of reference slice images may be representative of one of the plurality of slice locations in more than one frame of the plurality of frames. The at least one processor may be further configured to direct the system to reconstruct at least one slice image based on the plurality of aliasing images and the plurality of reference slice images. Each of the at least one slice image may be representative of one of the plurality of slice locations in one of the plurality of frames.

In some embodiments, the plurality of slice locations may include a first slice location and at least one second slice location. For PE steps that correspond to PE lines at a same location in K-space and are applied in a pair of frames of the plurality of frames, phase differences each of which is between the at least one second slice location and the first slice location in one PE step of the PE steps may be different.

In some embodiments, the at least one second slice location may include one second slice location. For the PE steps that correspond to PE lines at a same location in K-space and are applied in the pair of frames of the plurality of frames, the phase differences each of which is between the second slice location and the first slice location in one PE step of the PE steps may change by 180 degrees.

In some embodiments, the at least one second slice location may include two second slice locations. For the PE steps that correspond to PE lines at a same location in K-space and are applied in the pair of frames of the plurality of frames, the phase differences each of which is between the first slice location and one of the second slice locations in one PE step of the PE steps may change by 120 degrees. The phase differences each of which is between the first slice location and the other one of the second slice locations in one PE step of the PE steps may change by 240 degrees.

In some embodiments, during at least one frame of the plurality of frames, the phases of the at least one second slice location in each pair of consecutive PE steps of the plurality of PE steps may be different.

In some embodiments, the reconstruction of the at least one slice image based on the plurality of aliasing images and the plurality of reference slice images may be performed according to a parallel imaging reconstruction algorithm.

In some embodiments, during at least one PE step in at least one of the plurality of frames, a compensating magnetic field gradient may be applied along a slice-encoding direction after the readout of the corresponding echo signal. The compensating magnetic field gradient may have a same magnitude as and be in an opposite gradient direction to the phase modulation magnetic field gradient applied in the at least one PE step.

In some embodiments, during at least one PE step in at least one of the plurality of frames, a phase modulated radio frequency (RF) excitation pulse may be applied to excite the plurality of slice locations, and the phase modulation in the at least one PE step may be achieved by a combination of the phase modulated RF excitation pulse and the phase modulation magnetic field gradient applied in the at least one PE step.

In some embodiments, the plurality of PE steps may be applied by at least one of a balanced steady-state free precession (bSSFP) pulse sequence, a fast spin echo (FSE) pulse sequence, an echo planar imaging (EPI) pulse sequence, or a spoiled gradient echo (GRE) pulse sequence.

In some embodiments, during at least one PE step in at least one of the plurality of frames, the phase modulation magnetic field gradient may be applied along the slice-encoding direction after the plurality of slice locations are excited and before a readout of the corresponding echo signal.

According to one aspect of the present disclosure, a system for SMS MRI is provided. The system may include at least one storage device including a set of instructions, and at least one processor configured to communicate with the at least one storage device. When executing the set of instructions, the at least one processor may be configured to direct the system to perform the following operations. During each of a plurality of frames, the at least one processor may be configured to direct the system to cause an MRI scanner to apply a plurality of PE steps to each of a plurality of slice locations of a subject to acquire a set of echo signals. Each echo signal in the set of echo signals may correspond to a PE line in K-space. The plurality of slice locations may include a first slice location and at least one second slice location. The at least one processor may further be configured to direct the system to reconstruct at least one slice image based on the plurality of sets of echo signals acquired in the plurality of frames. Each of the at least one slice image may be representative of one of the plurality of slice locations in one of the plurality of frames. During each of at least some of the plurality of PE steps in each of the plurality of frames, a phase modulation magnetic field gradient may be applied, such that for PE steps that correspond to PE lines at a same location in K-space and are applied in a pair of frames of the plurality of frames, phase differences each of which is between the at least one second slice location and the first slice location in one PE step of the PE steps are different.

In some embodiments, for each of the plurality of frames, the at least one processor may be configured to direct the system to reconstruct an aliasing image representative of the plurality of slice locations in the frame based on the corresponding set of echo signals. The at least one processor may also be configured to direct the system to generate a plurality of reference slice images based on the plurality of aliasing images. Each of the plurality of reference slice images may be representative of one of the plurality of slice locations in more than one frame of the plurality of frames. The at least one processor may also be configured to direct the system to reconstruct the at least one slice image based on the plurality of aliasing images and the plurality of reference slice images.

According to another aspect of the present disclosure, a method for SMS MRI is provided. During each of a plurality of frames, the method may include causing an MRI scanner to apply a plurality of PE steps to each of a plurality of slice locations of a subject to acquire a set of echo signals. A phase modulation magnetic field gradient may be applied during each of at least some of the plurality of PE steps in the frame. For each of the plurality of frames, the method may include reconstructing an aliasing image representative of the plurality of slice locations in the frame based on the corresponding set of echo signals. The method may also include generating a plurality of reference slice images based on the plurality of aliasing images. Each of the plurality of reference slice images may be representative of one of the plurality of slice locations in more than one frame of the plurality of frames. The method may further include reconstructing at least one slice image based on the plurality of aliasing images and the plurality of reference slice images. Each of the at least one slice image may be representative of one of the plurality of slice locations in one of the plurality of frames.

According to another aspect of the present disclosure, a method for SMS MRI is provided. During each of a plurality of frames, the method may include causing an MRI scanner to apply a plurality of PE steps to each of a plurality of slice locations of a subject to acquire a set of echo signals. Each echo signal in the set of echo signals may correspond to a PE line in K-space. The plurality of slice locations may include a first slice location and at least one second slice location. The method may also include reconstructing at least one slice image based on the plurality of sets of echo signals acquired in the plurality of frames. Each of the at least one slice image may be representative of one of the plurality of slice locations in one of the plurality of frames. During each of at least some of the plurality of PE steps in each of the plurality of frames, a phase modulation magnetic field gradient may be applied, such that for PE steps that correspond to PE lines at a same location in K-space and are applied in a pair of frames of the plurality of frames, phase differences each of which is between the at least one second slice location and the first slice location in one PE step of the PE steps are different.

According to another aspect of the present disclosure, a non-transitory computer-readable storage medium including instructions for SMS MRI is provided. When accessed by at least one processor of a system, the instructions may cause the system to perform a method. During each of a plurality of frames, the method may include causing an MRI scanner to apply a plurality of PE steps to each of a plurality of slice locations of a subject to acquire a set of echo signals. A phase modulation magnetic field gradient may be applied during each of at least some of the plurality of PE steps in the frame. For each of the plurality of frames, the method may include reconstructing an aliasing image representative of the plurality of slice locations in the frame based on the corresponding set of echo signals. The method may also include generating a plurality of reference slice images based on the plurality of aliasing images. Each of the plurality of reference slice images may be representative of one of the plurality of slice locations in more than one frame of the plurality of frames. The method may further include reconstructing at least one slice image based on the plurality of aliasing images and the plurality of reference slice images. Each of the at least one slice image may be representative of one of the plurality of slice locations in one of the plurality of frames.

According to another aspect of the present disclosure, a non-transitory computer-readable storage medium including instructions for SMS MRI is provided. When accessed by at least one processor of a system, the instructions may cause the system to perform a method. During each of a plurality of frames, the method may include causing an MRI scanner to apply a plurality of PE steps to each of a plurality of slice locations of a subject to acquire a set of echo signals. Each echo signal in the set of echo signals may correspond to a PE line in K-space. The plurality of slice locations may include a first slice location and at least one second slice location. The method may also include reconstructing at least one slice image based on the plurality of sets of echo signals acquired in the plurality of frames. Each of the at least one slice image may be representative of one of the plurality of slice locations in one of the plurality of frames. During each of at least some of the plurality of PE steps in each of the plurality of frames, a phase modulation magnetic field gradient may be applied, such that for PE steps that correspond to PE lines at a same location in K-space and are applied in a pair of frames of the plurality of frames, phase differences each of which is between the at least one second slice location and the first slice location in one PE step of the PE steps are different.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for simultaneous multi-slice MRI according to some embodiments of the present disclosure;

FIG. 11 is a schematic diagram illustrating an exemplary bSSFP pulse sequence according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
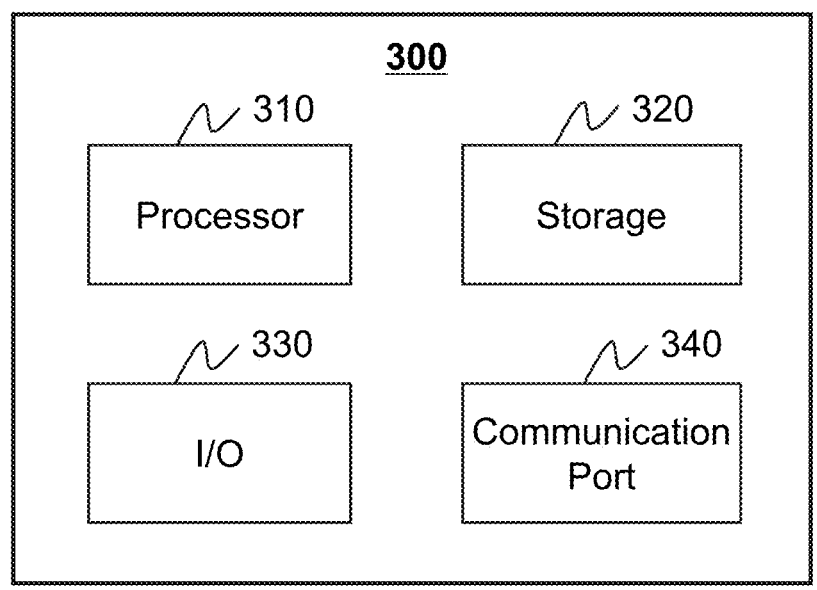
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. While the systems and methods disclosed in the present disclosure are described primarily regarding SMS in an MRI system. It should be understood that this is only for illustration purposes. The systems and methods of the present disclosure may be applied to any other kind of imaging system. In some embodiments, the imaging system may include a single modality imaging system and/or a multi-modality imaging system. The single modality imaging system may include, for example, the MRI system. The multi-modality imaging system may include, for example, an X-ray imaging-magnetic resonance imaging (X-ray-MRI) system, a single photon emission computed tomography-magnetic resonance imaging (SPECT-MRI) system, a digital subtraction angiography-magnetic resonance imaging (DSA-MRI) system, a computed tomography-magnetic resonance imaging (MRI-CT) system, a positron emission tomography-magnetic resonance imaging (PET-MRI) system, etc.

An aspect of the present disclosure relates to systems and methods for simultaneously imaging a plurality of slice locations of a subject using an MR scanner. The plurality of slice locations may include a first slice location and at least one second slice location. During each of a plurality of frames, the systems and methods may cause the MRI scanner to apply a plurality of phase-encoding (PE) steps to each of the slice locations to acquire a set of echo signals. During each of at least some of the PE steps in each of the frames, a phase modulation magnetic field gradient (also referred to as a phase modulation gradient for brevity) may be applied such that for PE steps that correspond to PE lines at a same location in K-space and are applied in a pair of frames of the plurality of frames, phase differences each of which is between the at least one second slice location and the first slice location in one PE step of the PE steps are different.

By applying the phase modulation gradients, the systems and methods may reconstruct, based on the sets of echo signals acquired in the frames without performing an additional reference scan, one or more slice images each of which may represent an individual slice location in one of the frames. For example, the systems and methods may reconstruct an aliasing image of the slice locations in each frame based on the corresponding set of echo signals, and generate reference slice images of the slice locations based on the aliasing images (e.g., by performing a linear combination of the aliasing images). The systems and methods may further reconstruct the slice image(s) based on the aliasing images and the reference slice images. In this way, the systems and methods may obviate the need for an additional reference scan, shortening the scan time, and/or improve the imaging efficiency and/or patient experience.

In addition, in some embodiments, the phase modulation herein may be achieved by phase modulation gradient(s) applied by a Z coil of the MR scanner alone or in combination with a phase modulated radio frequency (RF) excitation pulse. Conventional ways for phase modulation in auto-calibrating SMS during a plurality of frames, such as a controlled aliasing in parallel imaging results in higher acceleration (CAIPIRINHA) technique which merely uses a phase modulated RF excitation pulse, may be limited a pulse sequence without an echo train that only acquires one PE line of data per RF excitation pulse. The systems and methods provided in the present disclosure may be applicable to not only spoiled gradient echo (spGRE) sequences, but also balanced steady-state free precession (bSSFP) pulse sequences. The disclosed technique can also be applied to sequences with echo trains such as echo planar imaging (EPI) pulse sequences, and fast spin echo (FSE) pulse sequences.

Figure 1:
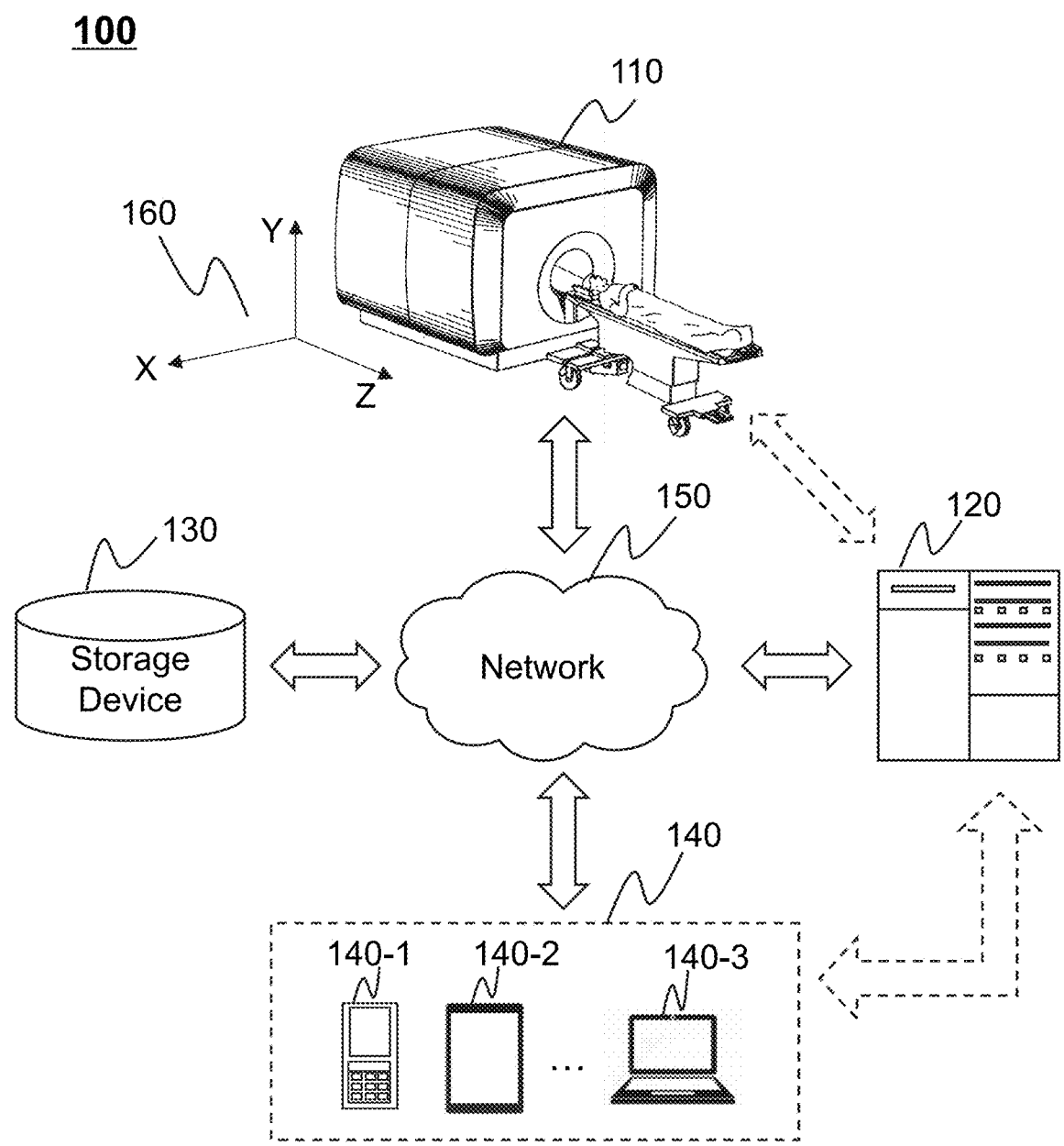
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MR scanner 110 (or referred to as an MRI scanner), a processing device 120, a storage device 130, one or more terminals 140, and a network 150. In some embodiments, the MR scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MR scanner 110 may be connected to the processing device 120 through the network 150. As another example, the MR scanner 110 may be connected to the processing device 120 directly.

The MR scanner 110 may be configured to scan a subject (or a part of the subject) to acquire image data, such as echo signals (or MR signals) associated with the subject. For example, the MR scanner 110 may detect a plurality of echo signals by applying an MR pulse sequence on the subject. In some embodiments, the MR scanner 110 may include, for example, a main magnet, a gradient coil (or also referred to a spatial encoding coil), a radio frequency (RF) coil, etc., as described in connection with FIG. 2. In some embodiments, the MR scanner 110 may be a permanent magnet MR scanner, a superconducting electromagnet MR scanner, or a resistive electromagnet MR scanner, etc., according to types of the main magnet. In some embodiments, the MR scanner 110 may be a high-field MR scanner, a mid-field MR scanner, and a low-field MR scanner, etc., according to the intensity of the magnetic field.

The subject scanned by the MR scanner 110 may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, cardiac, stomach, blood vessel, soft tissue, knee, feet, or the like, or a combination thereof.

For illustration purposes, a coordinate system 160 including an X axis, a Y-axis, and a Z-axis is provided in FIG. 1. The X axis and the Z axis shown in FIG. 1 may be horizontal, and the Y-axis may be vertical. As illustrated, the positive X direction along the X axis may be from the right side to the left side of the MRI scanner 110 seen from the direction facing the front of the MRI scanner 110; the positive Y direction along the Y axis shown in FIG. 1 may be from the lower part to the upper part of the MRI scanner 110; the positive Z direction along the Z axis shown in FIG. 1 may refer to a direction in which the subject is moved out of the scanning channel (or referred to as the bore) of the MRI scanner 110.

In some embodiments, the MR scanner 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the MRI scanner 110 may be found elsewhere in the present disclosure. See, e.g., FIG. 2 and the description thereof.

The processing device 120 may process data and/or information obtained from the MR scanner 110, the storage device 130, and/or the terminal(s) 140. For example, the MR scanner 110 may simultaneously excite a plurality of slice locations of the subject to acquire MR data from the slice locations. The processing device 120 may generate an aliasing image of the slice locations by processing the MR data collected by the MR scanner 110. Optionally, based on the aliasing image, the processing device 120 may reconstruct a plurality of slice images, each of which may represent one of the slice locations. In some embodiments, the processing device 120 may be a single server or a server group. The server group may be centralized or distributed. In some embodiments, the processing device 120 may be local or remote. For example, the processing device 120 may access information and/or data from the MR scanner 110, the storage device 130, and/or the terminal(s) 140 via the network 150. As another example, the processing device 120 may be directly connected to the MR scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MR scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MR scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MR scanner 110 to scan the subject from the user. As another example, the terminal(s) 140 may receive a processing result (e.g., a slice image representative of a slice location of the subject) from the processing device 120 and display the processing result to the user. In some embodiments, the terminal(s) 140 may be connected to and/or communicate with the MR scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MR scanner 110.

The network 150 may include any suitable network that can facilitate the exchange of information and/or data for the MRI system 100. In some embodiments, one or more components of the MRI system 100 (e.g., the MR scanner 110, the processing device 120, the storage device 130, the terminal(s) 140, etc.) may communicate information and/or data with one or more other components of the MRI system 100 via the network 150. For example, the processing device 120 may obtain image data (e.g., an echo signal) from the MR scanner 110 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MR scanner 110. As another example, a component of the MRI system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

Figure 2:
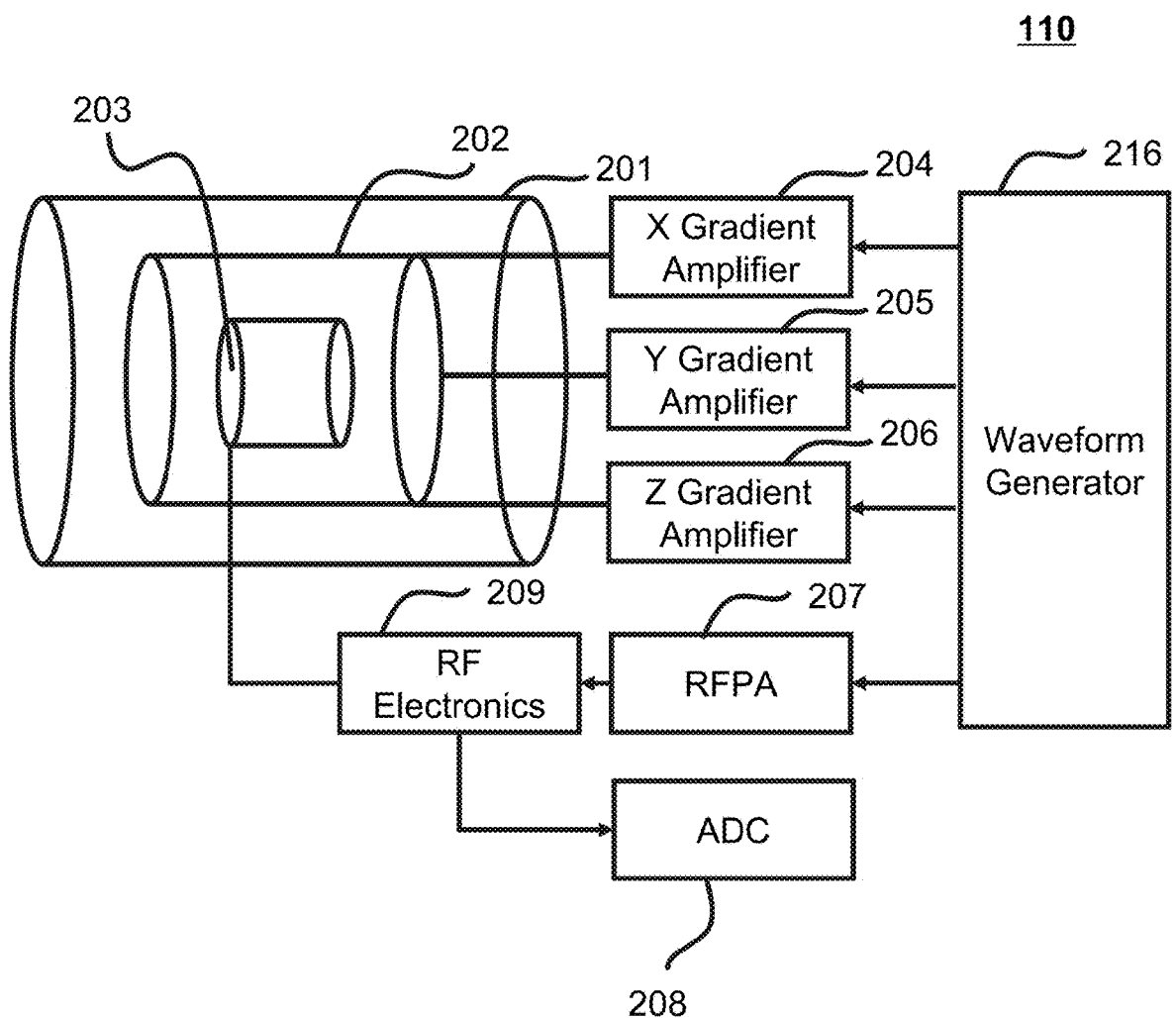
FIG. 2 is a schematic diagram illustrating an exemplary MRI scanner according to some embodiments of the present disclosure.

FIG. 2 is a schematic diagram illustrating an exemplary MRI scanner 110 according to some embodiments of the present disclosure. One or more components of the MRI scanner 110 are illustrated in FIG. 2. As illustrated, main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the subject is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203.

The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI scanner 110 may further include a subject positioning system (not shown). The subject positioning system may include a subject cradle and a transport device. The subject may be placed on the subject cradle and be positioned by the transport device within the bore of the main magnet 201.

MRI systems (e.g., the MRI system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

FIG. 3 is a schematic diagram illustrating exemplary hardware and/or software components of a computing device 300 according to some embodiments of the present disclosure. The computing device 300 may be used to implement any component of the MRI system 100 as described herein. For example, the processing device 120 and/or the terminal 140 may be implemented on the computing device 300, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data obtained from the MR scanner 110, the terminal(s) 140, the storage device 130, and/or any other component of the MRI system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MR scanner 110, the terminal(s) 140, the storage device 130, and/or any other component of the MRI system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure. For example, the storage 320 may store a program for the processing device 120 to execute for SMS imaging.

The I/O 330 may input and/or output signals, data, information, etc. In some embodiments, the I/O 330 may enable a user interaction with the processing device 120. In some embodiments, the I/O 330 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 150) to facilitate data communications. The communication port 340 may establish connections between the processing device 120 and the MR scanner 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
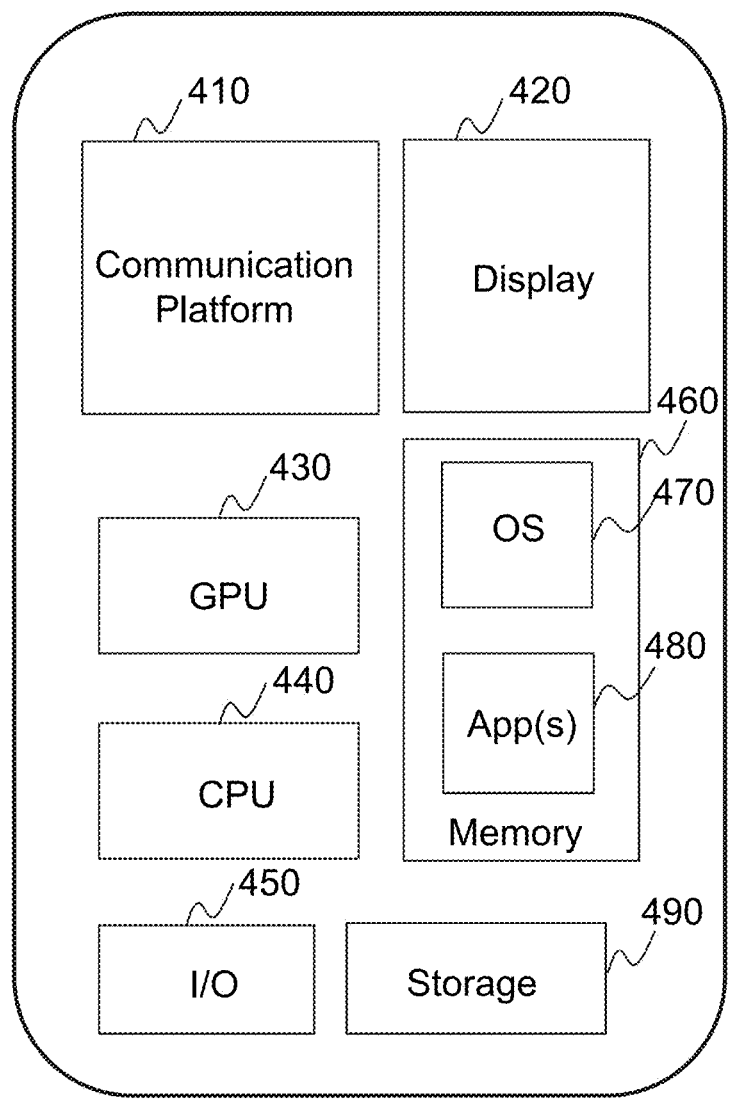
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 140 and/or the processing device 120) of the MRI system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
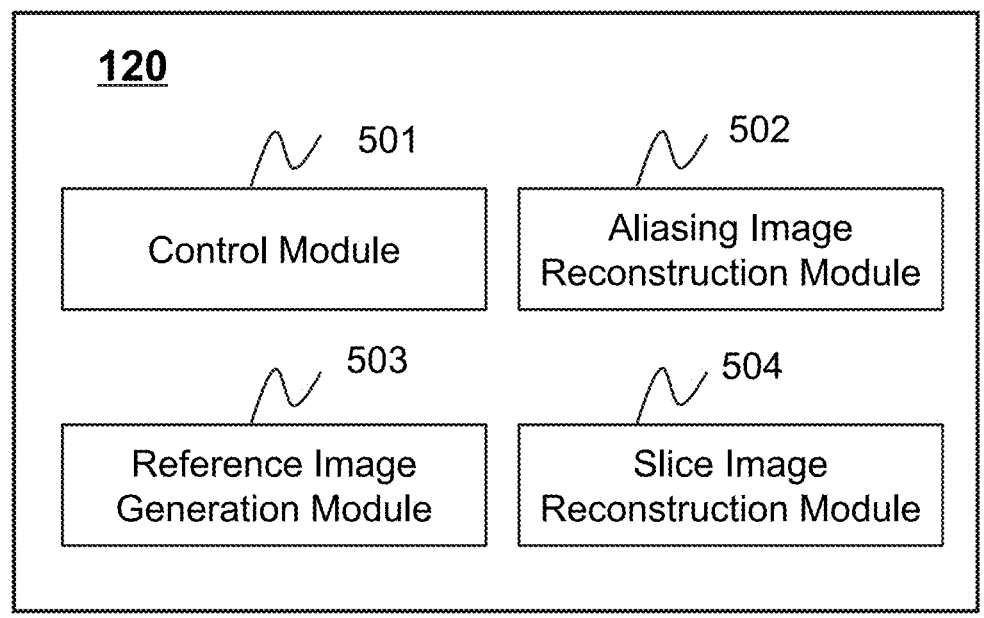
FIG. 5 is a block diagram illustrating an exemplary processing device according to some embodiments of the present disclosure.

FIG. 5 is a block diagram illustrating an exemplary processing device 120 according to some embodiments of the present disclosure. As shown in FIG. 5, the processing device 120 may include a control module 501, an aliasing image reconstruction module 502, a reference image generation module 503, and a slice image reconstruction module 504.

The control module 501 may be configured to control one or more components of the MRI system 100. For example, during each of a plurality of frames, the control module 501 may be configured to cause an MRI scanner to apply a plurality of PE steps to each of a plurality of slice locations of a subject (e.g., a patient) to acquire a set of echo signals. As used herein, a slice location of a subject may refer to a transverse plane of the subject that is parallel to an X-Y plane defined by the coordinate system 160. A frame may refer to a time segment with any duration. A PE step may refer to an individual acquisition step for spatial encoding along a phase-encoding direction. In some embodiments, during each of at least some of the PE steps in each frame, a phase modulation gradient may be applied by, for example, Z coils of the MR scanner along a slice encoding direction. More descriptions regarding the acquisition of the echo signals may be found elsewhere in the present disclosure. See, e.g., operation 601 in FIG. 6 and relevant descriptions thereof.

The aliasing image reconstruction module 502 may be configured to reconstruct an aliasing image representative of the slice locations of the subject in a frame based on the set of echo signals acquired in the frame. For example, the aliasing image reconstruction module 502 may sample the echo signals acquired in the frame and store the sampled data into a K-space matrix. The aliasing image reconstruction module 502 may further reconstruct the K-space matrix into the aliasing image of the frame by performing Fourier transformation. More descriptions regarding the reconstruction of an aliasing image may be found elsewhere in the present disclosure. See, e.g., operation 602 in FIG. 6 and relevant descriptions thereof.

The reference image generation module 503 may be configured to generate a plurality of reference slice images based on the plurality of aliasing images. A reference slice image refers to an image representative of one of the plurality of slice locations in more than one frame of the plurality of frames. In some embodiments, a reference slice image may be generated by performing a combination (e.g., a linear combination) on at least two of the aliasing images of the frames. More descriptions regarding the generation of a reference image may be found elsewhere in the present disclosure. See, e.g., operation 603 in FIG. 6 and relevant descriptions thereof.

The slice image reconstruction module 504 may be configured to reconstruct at least one slice image based on the aliasing images and the reference slice images. Each of the at least one slice image may be representative of one of the slice locations in one of the frames. In some embodiments, the at least one slice image may be reconstructed based on the aliasing images and the reference slice images according to a parallel imaging reconstruction algorithm. More descriptions regarding the reconstruction of a slice image may be found elsewhere in the present disclosure. See, e.g., operation 604 in FIG. 6 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may include one or more additional modules, such as a storage module (not shown) for storing data. As another example, one or more modules of the processing device 120 described above may be omitted. Additionally or alternatively, two or more modules of the processing device 120, such as the aliasing image reconstruction module 502 and the reference image generation module 503, may be integrated into a single component. A module of the processing device 120 may be divided into two or more units.

FIG. 6 is a flowchart illustrating an exemplary process for simultaneous multi-slice MRI according to some embodiments of the present disclosure. In some embodiments, process 600 may be executed by the MRI system 100. For example, the process 600 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 600.

In some embodiments, the process 600 may be performed to simultaneously image a plurality of slice locations of a subject (e.g., a patient, a specific organ of the patient, a man-made object) using an MRI scanner. As used herein, a slice location of a subject may refer to a transverse plane of the subject that is parallel to an X-Y plane defined by the coordinate system 160. The count of the imaged slice locations may be equal to any positive number, such as two, three, four, five, etc. The imaged slice locations may be located at any position of the subject. The MR scanner that performs the simultaneous imaging may include one or more similar components to the MR scanner 110 as described in connection with FIGS. 1 and 2. For example, the MR scanner may include a main magnet, three sets of gradient coils, an RF coil, or the like, or any combination thereof. The three sets of gradient coils may be configured to generate magnetic gradient fields Gx, Gy, and Gz in the X direction, the Y direction, and the Z direction defined by the coordinate system 160, respectively. For illustration purposes, one of the plurality of slice locations may be considered as a first slice location and the other slice location(s) may be considered as at least one second slice location. The first slice location may be any slice location selected from the slice locations. In some embodiments, the first slice location may pass through an isocenter of the MRI scanner.

In 601, during each of a plurality of frames, the processing device 120 (e.g., the control module 501, processing circuits of the processor 310) may cause the MRI scanner to apply a plurality of PE steps to each of the slice locations of the subject to acquire a set of echo signals.

As used herein, a frame may refer to a time segment with any duration. The plurality of frames may be consecutive or inconsecutive frames. Different frames may have a same duration or different durations. A PE step may refer to an individual acquisition step for spatial encoding along a phase-encoding direction. Each PE step in a frame may acquire an echo signal from the excited slice locations, wherein the acquired echo signal may be stored as a PE line in a single row of a K-space matrix corresponding to the frame. The K-space matrix corresponding to the frame may be a two-dimensional matrix that has a Kx axis along the frequency-encoding direction and a Ky axis along the phase-encoding direction. The K-space matrix corresponding to the frame may be used for reconstructing an aliasing image corresponding to the frame, which is described in detail in connection with operation 602.

In some embodiments, the matrix size of the K-space matrix corresponding to a certain frame may be associated with the resolution of the aliasing image of the frame to be reconstructed. For example, to reconstruct an aliasing image having a resolution of 256*128, a 256*128 K-space matrix may need to be generated. That is, 256 PE steps may need to be applied in the certain frame to fill 256 PE lines of the K-space matrix. The duration of the certain frame may be determined based on the count (or number) of the PE steps and a unit duration of each of the PE steps. In some embodiments, the K-space matrixes corresponding to the plurality of frames may have a same matrix size. The PE lines located at a same row in the K-space matrixes of different frames may be regarded as being located at a same location in K-space. The PE steps that correspond to PE lines located at a same location in K-space and are applied in different frames may be regarded as being corresponding to each other.

In some embodiments, during a frame, the plurality of PE steps may be performed by applying a certain pulse sequence. For example, a first pulse sequence without an echo train may be applied. The first pulse sequence may include a plurality of RF excitation pulses and only one echo signal (i.e., data corresponding to a single PE line) may be acquired after each RF excitation pulse. Exemplary first pulse sequences without an echo train may include bSSFP and spoiled GRE pulse sequences, or the like. In some embodiments, each RF excitation pulse in the first pulse sequence may be a multi-band RF pulse, which may be applied at the same time with a slice-selection gradient to simultaneously excite the plurality of slice locations to be imaged.

As another example, a second pulse sequence with an echo train may be applied in a frame to perform the corresponding PE steps. The second pulse sequence may acquire a plurality of echo signals (i.e., data corresponding to a plurality of PE lines) after each single RF excitation pulse. Exemplary second pulse sequences with an echo train may include an EPI pulse sequence, an FSE pulse sequence, or the like. In some embodiments, different pulse sequences may be suitable for scanning different subjects. For example, an EPI pulse sequence may be applied to scan the brain of a patient.

In 602, for each of the frames, the processing device 120 (e.g., the aliasing image reconstruction module 502, the processing circuits of the processor 310) may reconstruct an aliasing image representative of the slice locations in the frame based on the corresponding set of echo signals.

In some embodiments, for each frame, the processing device 120 may sample the set of echo signals acquired in the frame and store the sampled data into a K-space matrix corresponding to the frame as aforementioned. The processing device 120 may further reconstruct the K-space matrix corresponding to the frame into the aliasing image of the frame by performing Fourier transformation. The reconstructed aliasing image may include an aliasing artifact, i.e., aliasing pixels. In order to reduce the aliasing artifacts in the aliasing images and facilitate slice separation based on the aliasing images, it may be desirable that, in each reconstructed aliasing image, the portions of the reconstructed aliasing image corresponding to different slice locations of the subject have a preset field of view (FOV) shift with respect to each other. For example, for an aliasing image of two slice locations having a resolution of 128*128, it is desirable that the portions corresponding to the two slice locations in the aliasing image have a half FOV shift with respect to each other, e.g., a 64-pixel shift along the phase-encoding direction. As another example, for an aliasing image of three slice locations having a resolution of 128*300, it is desirable that the portions corresponding to every two adjacent slice locations in the aliasing image have a one third FOV shift with respect to each other, e.g., a 100-pixel shift along the phase-encoding direction. In some embodiments, the preset FOV shift may be a default setting of the MRI system 100 or set manually by a user of the MRI system 100 via, e.g., a terminal (e.g., the terminal 140). Alternatively, the preset FOV shift may be determined by the processing device 120 based on, for example, the count of the slice locations to be imaged, a distance between different slice locations, the sensitivity of an RF coil (e.g., the RF coil 203) for echo signal detection, or the like, or any combination thereof.

To achieve the preset FOV shift in the aliasing image of a frame, a plurality of phase modulation gradients may be applied by the gradient coils (e.g., Z coils) of the MR scanner along the slice-encoding direction (i.e., the Z direction of the coordinate system 160) in the frame. For example, during each of the PE steps (or a portion thereof) in the frame, a phase modulation gradient may be applied by the Z-coils of the MR scanner along the slice-encoding direction after the slice locations are excited and before a readout of the corresponding echo signal. Due to the phase modulation gradient applied in a PE step, each of the slice locations may have a specific phase when the corresponding echo signal is acquired.

Figure 7:
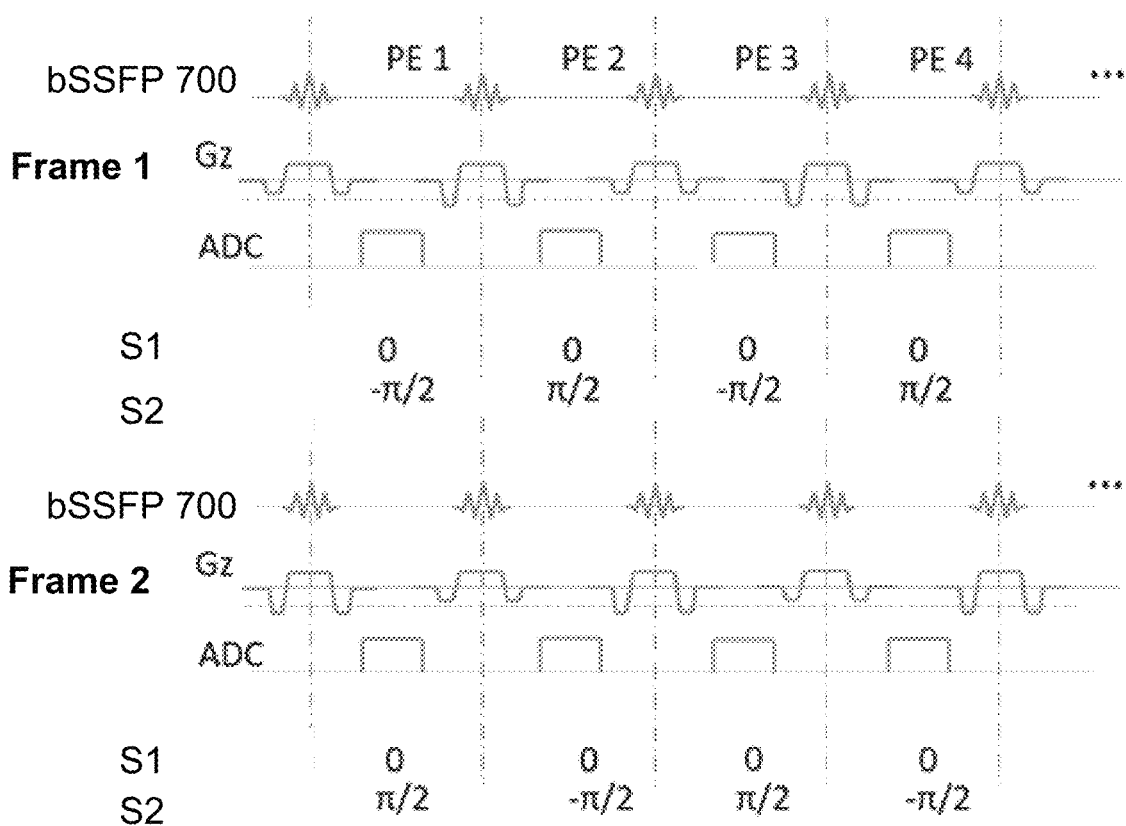
FIG. 7 is a schematic diagram illustrating an exemplary bSSFP pulse sequence according to some embodiments of the present disclosure.

In some embodiments, the phase modulation gradients applied in a frame may be designed so as to obviate the need for an additional reference scan of the slice locations. For example, for corresponding PE steps that are applied in a pair of frames of the plurality of frames, phase differences between a second slice location and the first slice location are different, wherein the pair of frames may be two consecutive frames or inconsecutive frames among the plurality of frames. Merely by way of example, as illustrated in FIG. 7, during each of the first PE steps in Frame 1 and Frame 2, a phase modulation gradient may be applied such that the phase difference between slice locations S1 and S2 changes from −90° in Frame 1 to 90° in Frame 2. As another example, as illustrated in FIG. 11, a phase modulation gradient may be applied during the first PE step in Frame 3 such that the phase difference between slice locations S3 and S4 changes from −120° in Frame 3 to 0° in Frame 4, and the phase difference between slice locations S3 and S5 changes from −240° in Frame 3 to 0° in Frame 4.

In some embodiment, during at least one PE step in at least one of the frames, a compensating magnetic field gradient may be applied along the slice-encoding direction after the readout of the corresponding echo signal. The compensating magnetic field gradient may have a same magnitude as and being in an opposite gradient direction to the phase modulation gradient applied in the at least one PE step. This may eliminate or reduce an effect of the phase modulation gradient applied in the at least one PE step on the echo signal acquisition in a next PE step. In some embodiments, in each PE step in which a phase modulation gradient is applied, a compensating magnetic field gradient may be applied after the readout of the corresponding echo signal. For example, during a frame in which a bSSFP pulse sequence is applied, a compensating magnetic field gradient may be applied in each PE step in the frame. Alternatively, the PE steps in a frame, e.g., in which a spoiled GRE pulse sequence is applied, may be performed without a compensating magnetic field gradient.

In some embodiments, a phase modulated RF excitation pulse may be applied in at least one PE step in at least one frame to excite the plurality of slice locations, and the phase modulation in the at least one PE step may be achieved by a combination of the phase modulated RF excitation pulse and the phase modulation gradient applied in the at least one PE step. For example, to achieve a 180-degree phase difference between a second slice location and the first slice location in a PE step, a 90-degree phase difference may be achieved by the phase modulated RF excitation pulse, and the other 90-degree phase difference may be achieved by the phase modulation gradient. More descriptions regarding a configuration of a pulse sequence applied in a frame may be found elsewhere in the present disclosure. See, e.g., FIGS. 7-14 and relevant descriptions thereof.

In 603, the processing device 120 (e.g., the reference image generation module 503, the processing circuits of the processor 310) may generate a plurality of reference slice images based on the plurality of aliasing images.

As used herein, a reference slice image refers to an image representative of one of the plurality of slice locations in more than one frame of the plurality of frames. A reference slice image may have a lower temporal resolution than the aliasing images reconstructed in 602 and slice image(s) to be reconstructed in 604. For example, an aliasing image may correspond to a single frame, while a reference slice image may be generated based on more than one aliasing image, thereby having a lower temporal resolution.

In some embodiments, a reference slice image may be generated by performing a combination (e.g., a linear combination) on at least two of the aliasing images reconstructed in 602. For example, four aliasing images (including a first, second, third, and fourth aliasing images) corresponding to four frames (including a first, second, third, and fourth frames) may be reconstructed in 602. A reference slice image of a certain slice location may be generated by performing a combination of at least two of the four aliasing images. Merely by way of example, a reference slice image R1 of the first slice location may be generated by adding the first and second aliasing images or subtracting the first aliasing image from the second aliasing image. The reference slice image R1 may correspond to the first and second frames and have a lower temporal resolution than the original four aliasing images. As another example, a reference slice image R2 of the first slice location may be a weighted sum of the first, second and third aliasing images. The reference slice image R2 may correspond to the first, second, and third frames and have a lower time resolution than the original four aliasing images. In some embodiments, an average of the reference slice images R1 and R2 may be determined as a final reference slice image of the first slice location.

In 604, the processing device 120 (e.g., the slice image reconstruction module 504, the processing circuits of the processor 310) may reconstruct at least one slice image based on the aliasing images and the reference slice images. Each of the at least one slice image may be representative of one of the slice locations in one of the frames. The at least one slice image may have a time resolution same as the aliasing images as described in connection with 602. As used herein, "based on the aliasing images and the reference slice images" refers to "based on at least a portion of the aliasing images and at least a portion of the reference slice images."

The reconstruction of the at least one slice image may be performed based on the aliasing images and the reference slice images according to a parallel imaging reconstruction algorithm, for example, a slice-generalized autocalibrating partial parallel acquisition (GRAPPA) algorithm, a simultaneous acquisition of spatial harmonics (SMASH) algorithm, a sensitivity encoding (SENSE) algorithm, or the like. In some embodiments, for each slice location in each frame, a corresponding slice image may be reconstructed in 604. Merely by way of example, if there are two slice locations and two frames, four slice images may be reconstructed. Alternatively, only a portion of the four slice images may be reconstructed in 604. Merely by way of example, in 604, one slice image of the first slice location in one frame may be reconstructed based on the aliasing image of the frame and the reference slice image of the first slice location according to the GRAPPA algorithm.

In some embodiments, the subject may undergo a physiological motion during the plurality of frames. For example, the subject may include the heart of a patient that undergoes a cardiac motion. A plurality of slice locations in the heart of the patient may be imaged to generate a series of slice images of each slice location in a plurality of cardiac phases. For a slice location in the heart of the patient, the corresponding slice images may dynamically illustrate the cardiac motion of the slice location along the temporal dimension in different cardiac phases. In some embodiments, the subject may undergo little or no physiological motion during the plurality of frames. For example, the subject may include the brain of a patient. A plurality of slice locations in the brain of the patient may be imaged to generate a series of slice images of each slice location. For a slice location in the brain of the patient, the corresponding slice images may dynamically illustrate a change (e.g., a change in the amount of blood flow) in an activated region in the brain.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, the process 600 may include an additional operation to transmit the slice images to a terminal device (e.g., a terminal device 140 of a doctor) for display. In some embodiments, two or more operations of the process 600 may be integrated into a single operation, and/or a single operation of the process 600 may be divided into two operations. Merely by way of example, operations 602 to 604 may be integrated into a single operation in which the processing device 120 may reconstruct the slice images based on the plurality of sets of echo signals acquired in 601. In some embodiments, a single reference slice image of a certain slice location may be regenerated in 603 to reconstruct slice image(s) of the certain slice location in 604.

FIG. 7 is a schematic diagram illustrating an exemplary bSSFP pulse sequence 700 according to some embodiments of the present disclosure. The bSSFP pulse sequence 700 may be applied by an MR scanner (e.g., the MR scanner 110) to simultaneously imaging a slice location S1 and a slice location S2 of a subject. As shown in FIG. 7, the bSSFP pulse sequence 700 may be applied in Frame 1 and Frame 2 with different modulation strategies. During each of the Frames 1 and 2, a plurality of PE steps (e.g., PE1, PE2, PE3, and PE4 as shown in FIG. 7) may be applied to the slice locations S1 and S2 to obtain a corresponding set of echo signals.

For illustration purposes, the application of the bSSFP pulse sequence 700 in Frame 1 is described hereinafter as an example. In each PE step in Frame 1, an excitation RF pulse (e.g., a multi-band RF pulse) may be applied with a slice-selection gradient to simultaneously excite the slice locations S1 and S2, and an echo signal may be acquired from the slice locations S1 and S2. The echo signal acquired in each PE step in Frame 1 may be stored as a PE line in a K-space matrix corresponding to Frame 1. An aliasing image A1 of the slice locations S1 and S2 corresponding to Frame 1 may be reconstructed by performing Fourier transformation on the K-space matrix corresponding to Frame 1.

In some embodiments, during each PE step in Frame 1, a phase modulation gradient may be applied by Z coils of the MR scanner after an excitation of the slice locations S1 and S2 and before a readout of the corresponding echo signal, so as to impart a preset FOV/2 shift between the portions corresponding to the slice locations S1 and S2 in the aliasing image A1. For example, the slice location S1 may be located at an isocenter of the MR scanner, and the phase of the slice location S1 in different PE steps in Frame 1 may be always equal to 0°. Due to the phase modulation gradients applied in the PE steps in Frame 1, the phase of the slice location S2 may alternate between −90° and 90° along the phase encoding direction, and the phase difference between the slice locations S1 and S2 may alternate between 90° and −90° along the phase encoding direction. In some embodiments, the intensity of the phase modulation gradient applied in a PE step may be determined according to the preset FOV shift, a distance between the slice locations S1 and S2, a gyromagnetic ratio of the subject, an amplitude of the phase modulation gradient, a duration of the phase modulation gradient, or the like, or any combination thereof.

Ideally, in a PE step in Frame 1, the phase modulation of the slice locations S1 and S2 may be adjusted to 0 after a readout of the corresponding echo signal and before a next excitation of the slice locations S1 and S2, in order to eliminate or reduce an effect of the phase modulation gradient on the echo signal acquisition in a next PE step. To this end, in some embodiments, a compensating magnetic field gradient may be applied along the slice-encoding direction in the PE step in Frame 1 after the readout of the corresponding echo signal. The compensating magnetic field gradient applied in the PE step may have a same magnitude as and be in an opposite gradient direction to the phase modulation gradient applied in the PE step. For example, in a certain PE step in Frame 1, the phase of the slice location S2 is equal to −90° after a phase modulation gradient is applied. A compensating magnetic field gradient may be applied to change the phase of the slice location S2 by 90° to reach 0° after the readout of the corresponding echo signal and before an application of a next excitation RF pulse.

The application of the bSSFP pulse sequence 700 in Frame 2 may be similar to that of the bSSFP pulse sequence 700 Frame 1, except that the phase modulation gradients applied in each PE steps of Frame 2 may be different, such that for corresponding PE steps in Frames 1 and 2, the phase differences between the slice locations S1 and S2 are different. Merely by way of example, as shown in FIG. 7, the phase of the slice location S2 in Frame 2 alternates between 90° and −90° along the phase encoding direction, and the phase difference between the slice locations S1 and S2 in Frame 2 may alternate between −90° and 90° the phase encoding direction. For the PE steps that correspond to PE lines at a same location in K-space and are applied in Frames 1 and 2, the phase difference between the slice locations S1 and S2 may change by 180°. Taking the first PE steps applied in Frames 1 and 2 for example, the phase difference between the slice locations S1 and S2 changes from −90° in Frame 1 to 90° in Frame 2.

In some embodiments, the processing device 120 may reconstruct the aliasing image A1 of the slice locations S1 and S2 corresponding to Frame 1 based on the echo signals obtained in Frame 1, and an aliasing image A2 of the slice locations S1 and S2 corresponding to Frame 2 based on the echo signals obtained in Frame 2 by performing, e.g., operation 602. Due to the phase modulation in Frames 1 and 2, the aliasing image A1 may be regarded as a summation of the slice locations S1 and S2, and the aliasing image A2 may be regarded as a difference between the slice locations S1 and S2. The aliasing images A1 and A2 may be represented by Equation (1) and Equation (2), respectively, as below:

$$A1 = S1 + S1, \quad \text{Equation (1)}$$

$$A2 = S1 - S2. \quad \text{Equation (2)}$$

A reference slice image F1 representative of the slice location S1 in Frames 1 and 2, and a reference slice image F2 representative of the slice location S2 in Frames 1 and 2 may be determined by linearly combining the aliasing images A1 and A2 according to Equations (3) and (4), respectively, as below:

$$F1 = \frac{(A1 + A2)}{2}, \quad \text{Equation (3)}$$

$$F2 = \frac{(A1 - A2)}{2}. \quad \text{Equation (4)}$$

The reference slice images F1 and F2 may have a lower temporal resolution than the aliasing images A1 and A2. The processing device 120 may further reconstruct one or more slice images of the slice locations S1 and S2 based on the aliasing images A1 and A2 and the reference slice images F1 and F2. For example, based on the aliasing image A1, the reference slice image F1, and the reference slice image F2, the processing device 120 may reconstruct a slice image of each of the slice locations S1 and S2 in Frame 1 using a parallel imaging reconstruction algorithm. Similarly, based on the aliasing image A2, the reference slice image F1, and the reference slice image F2, the processing device 120 may reconstruct a slice image of each of the slice locations S1 and S2 in Frame 2.

Figure 8A:
FIGS. 8A and 8B illustrate exemplary aliasing images of two slice locations in the heart according to some embodiments of the present disclosure.
Figure 8B:
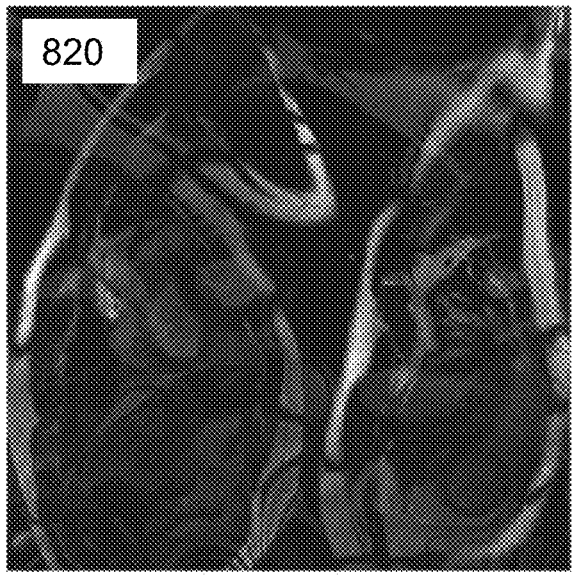
Figure 9A:
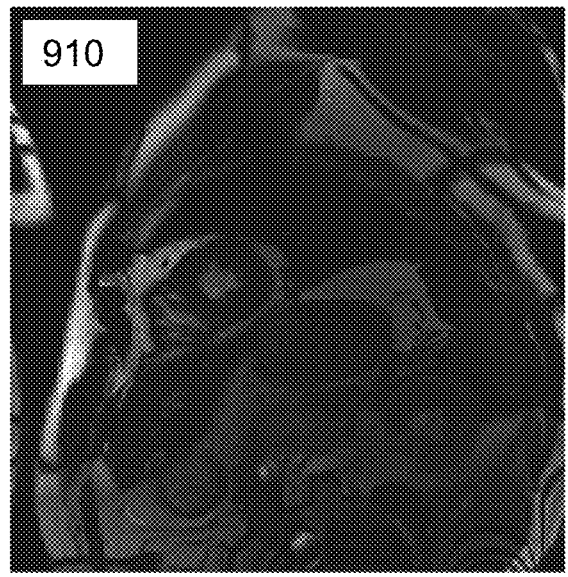
FIGS. 9A and 9B illustrate exemplary reference slice images of two slice locations in the heart according to some embodiments of the present disclosure.
Figure 9B:
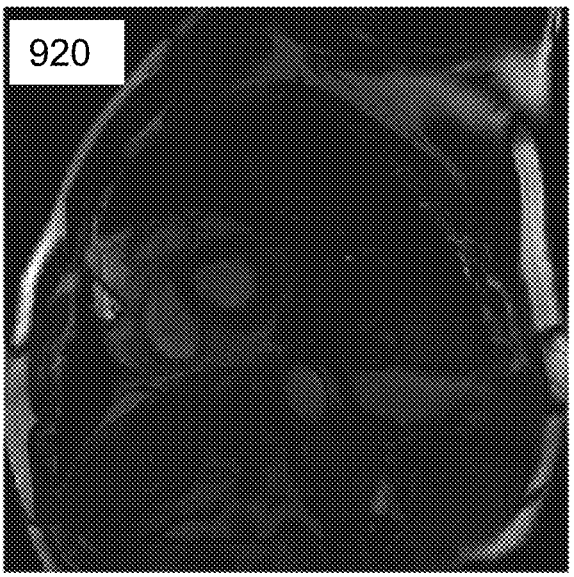
Figure 10:
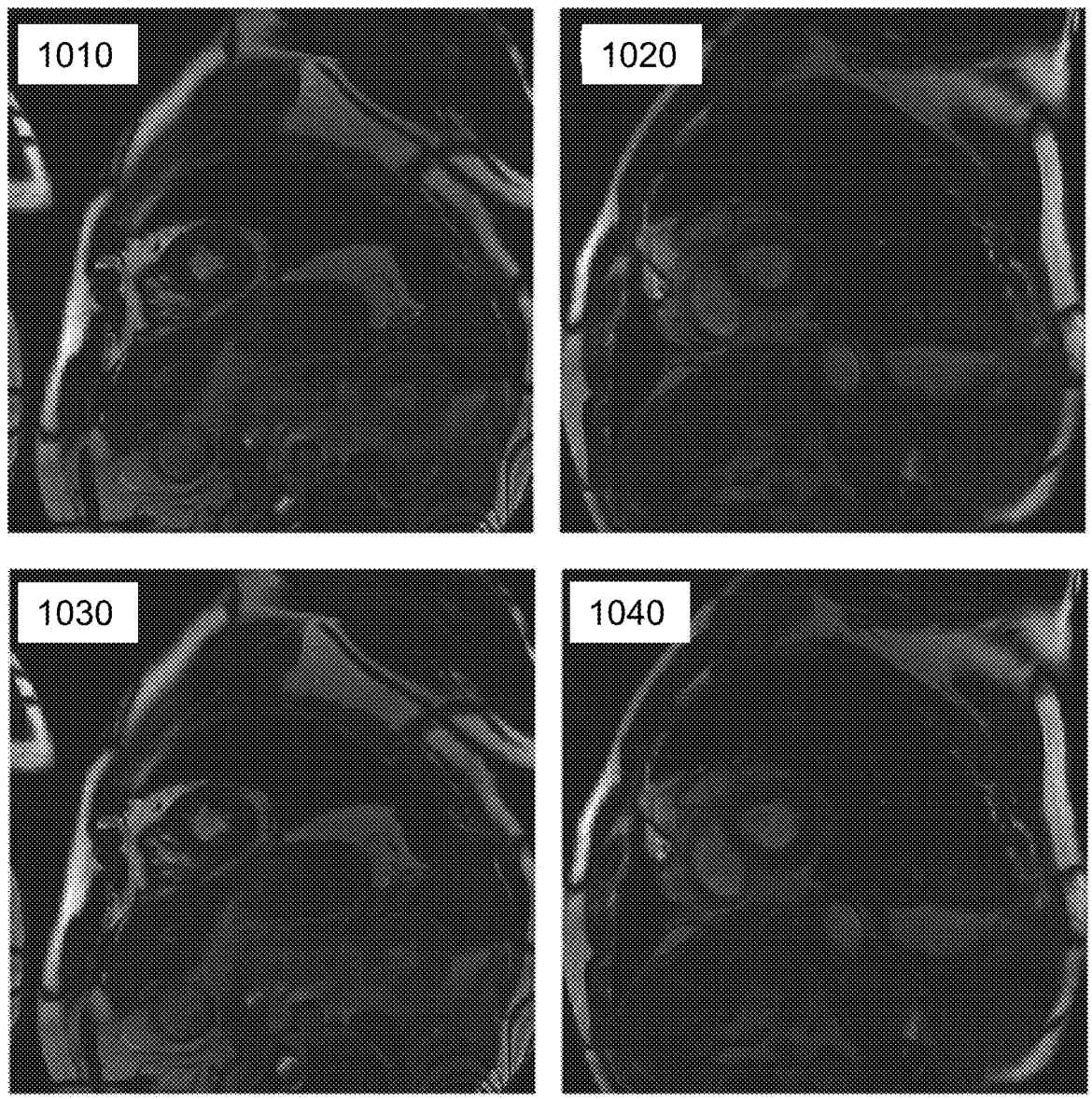
FIG. 10 illustrates exemplary cardiac slice images according to some embodiments of the present disclosure.

In some embodiments, the bSSFP pulse sequence 700 illustrated in FIG. 7 may be applied to slice locations S1 and S2 in the heart of a patient for SMS cardiac MRI. For illustration purposes, FIG. 8A illustrates an exemplary aliasing image 810 of the slice locations S1 and S2 in the heart acquired in Frame 1 according to some embodiments of the present disclosure. FIG. 8B illustrates an exemplary aliasing image 820 of the slice locations S1 and S2 in the heart acquired in Frame 2 according to some embodiments of the present disclosure. FIG. 9A illustrates an exemplary reference slice image 910 of the slice location S1 in Frames 1 and 2 according to some embodiments of the present disclosure. FIG. 9B illustrates an exemplary reference slice image 920 of the slice location S2 in Frames 1 and 2 according to some embodiments of the present disclosure. FIG. 10 illustrates an exemplary slice image 1010 of the slice location S1 in Frame 1, an exemplary slice image 1020 of the slice location S2 in Frame 1, an exemplary slice image 1030 of the slice location S1 in Frame 2, and an exemplary slice image 1040 of the slice location S2 in Frame 2 according to some embodiments of the present disclosure.

FIG. 11 is a schematic diagram illustrating an exemplary bSSFP pulse sequence 1100 according to some embodiments of the present disclosure. The bSSFP pulse sequence 1100 may be applied by an MR scanner (e.g., the MR scanner 110) to simultaneously imaging slice locations S3, S4, and S5 of a subject. As shown in FIG. 11, the bSSFP pulse sequence 1100 may be applied in Frame 3, Frame 4, and Frame 5 with different modulation strategies. It should be noted that the terms "slice location Sn" and "Frame n" are used herein for the convenience of descriptions, and not intended to be limiting. For example, Frame 3 may be a same frame as or a different frame from Frame 1 as described in connection with FIG. 7. As another example, slice location S3 may be a same slice location as or a different slice location from slice location S1 as described in connection with FIG. 7.

The application of the bSSFP pulse sequence 1100 in a frame may be similar to that of the bSSFP pulse sequence

700 in a frame as described in connection with FIG. 7, except that the phase modulation applied with the bSSFP pulse sequence 1100 may be different from that of the bSSFP pulse sequence 700. Taking Frame 3 as an example, a phase modulation gradient may be applied in each of the first, third, fourth, sixth, etc., PE steps after an excitation of the slice locations S3, S4, and S5 and before a readout of the corresponding echo signal. Due to the phase modulation gradients applied in Frame 3, the phase of the slice location S4 may change from −120° to 0° to 120° periodically along the phase encoding direction, and the phase difference between the slice locations S3 and S4 may change from −120° to 0° to 120° periodically along the phase encoding direction in Frame 3. The phase of the slice location S5 may change from −240° to 0° to 240° periodically along the phase encoding direction, and the phase difference between the slice locations S3 and S5 may change from −240° to 0° to 240° periodically along the phase encoding direction in Frame 3. The phase modulation gradients applied in Frame 3 may impart a preset FOV/3 shift adjacent slices in an aliasing image A3 corresponding to Frame 3 reconstructed based on the echo signals acquired in Frame 3.

The application of the bSSFP pulse sequence 1100 in Frames 4 and 5 may be similar to that of the bSSFP pulse sequence 1100 in Frame 3, except that the phase modulation gradients applied in the three frames may be different from each other. In this way, for corresponding PE steps in a pair of frames of Frames 3, 4, and 5, the phase differences between the slice locations S3 and S4 may be different, and/or the phase differences between the slice locations S3 and S5 may be different. Merely by way of example, the phase difference between S3 and S4 in the first PE step in Frame 3 may be equal to −120°, which changes to 0° in the first PE step in Frame 4 and 120° in the first step in Frame 5. As another example, the phase difference between S3 and S5 in the first PE step in Frame 3 may be equal to −240°, which changes to 0° in the first PE step in Frame 4 and 240° in the first step in Frame 5.

In some embodiments, the processing device 120 may reconstruct an aliasing image A3 of the slice locations S3, S4, and S5 corresponding to Frame 3 based on the echo signals obtained in Frame 3, an aliasing image A4 of the slice locations S3, S4, and S5 corresponding to Frame 4 based on the echo signals obtained in Frame 4, and an aliasing image A5 of the slice locations S3, S4, and S5 corresponding to Frame 5 based on the echo signals obtained in Frame 5. Due to the phase modulations in Frames 3, 4, and 5, the aliasing images A3, A4, and A5 may be represented by Equation (5), Equation (6), and Equation (7), respectively, as below:

$$A3 = S3 + S4 + S5,\quad\text{Equation (5)}$$

$$A4 = S3 + \exp\left(\frac{2\pi}{3}i\right)S4 + \exp\left(\frac{4\pi}{3}i\right)S5,\quad\text{Equation (6)}$$

$$A5 = S3 + \exp\left(-\frac{2\pi}{3}i\right)S4 + \exp\left(-\frac{4\pi}{3}i\right)S5.\quad\text{Equation (7)}$$

A reference slice image F3 representative of the slice location S3 in Frames 3 to 5, a reference slice image F4 representative of the slice location S4 in Frames 3 to 5, and a reference slice image F5 representative of the slice location S5 in Frames 3 to 5 may be determined by linearly combining the aliasing images A3, A4, and A5 according to Equations (8), (9), and (10), respectively, as below:

$$F3 = \frac{(A3 + A4 + A5)}{3},\quad\text{Equation (8)}$$

$$F4 = \frac{A3 + \exp\left(-\frac{2\pi}{3}i\right)A4 + \exp\left(\frac{2\pi}{3}i\right)A5}{3},\quad\text{Equation (9)}$$

$$F5 = \frac{A3 + \exp\left(-\frac{4\pi}{3}i\right)A4 + \exp\left(\frac{4\pi}{3}i\right)A5}{3}.\quad\text{Equation (10)}$$

The reference slice images F3, F4, and F5 may have a lower temporal resolution than the aliasing images A3, A4, and A5. The processing device 120 may further reconstruct one or more slice images of the slice locations S3, S4, and S5 based on the aliasing images A3 to A5 and the reference slice images F3 to F5. For example, based on the aliasing image A3 and the reference slice images F3, F4, and F5, the processing device 120 may reconstruct a slice image for each of the slice locations S3, S4, and S5 in Frame 3.

Figure 12:
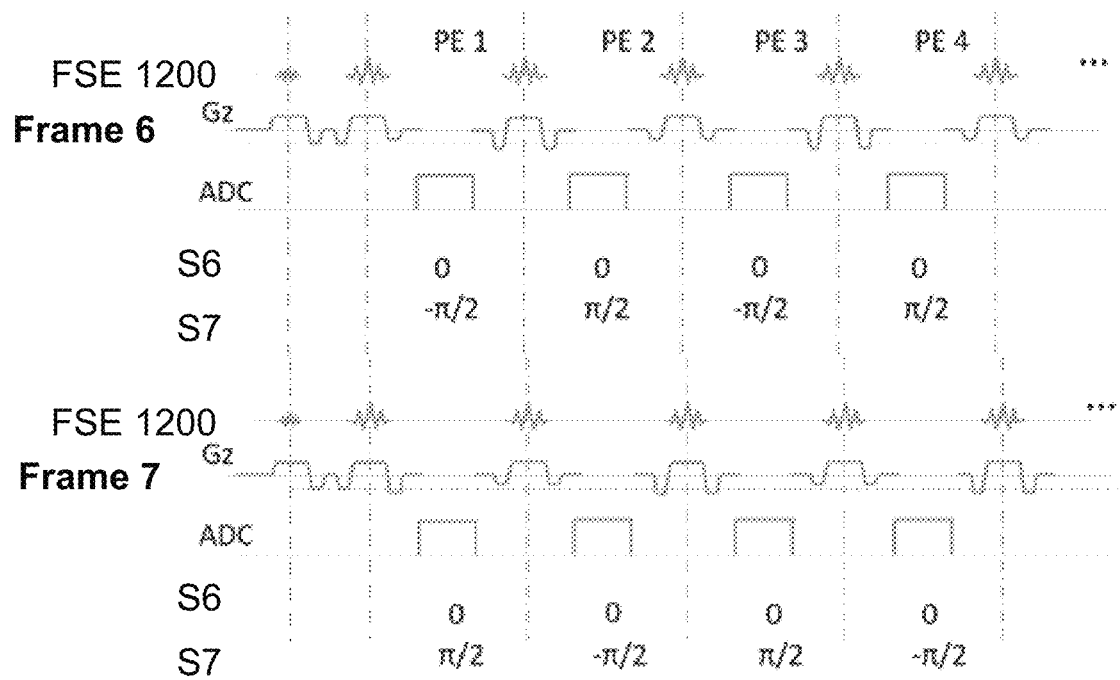
FIG. 12 is a schematic diagram illustrating an exemplary FSE pulse sequence according to some embodiments of the present disclosure.

FIG. 12 is a schematic diagram illustrating an exemplary FSE pulse sequence 1200 according to some embodiments of the present disclosure. The FSE pulse sequence 1200 may be applied by an MR scanner (e.g., the MR scanner 110) to simultaneously imaging a slice location S6 and a slice location S7 of a subject. As shown in FIG. 12, the FSE pulse sequence 1200 may be applied in Frame 6 and Frame 7 with different modulation strategies. During each of the Frames 6 and 7, a series of 180° refocusing pulses may be used after a single RF excitation pulse to perform a plurality of PE steps and obtain a corresponding train of echo signals.

Similar to a bSSFP pulse sequence 700 as described in connection with FIG. 7, a phase modulation gradient may be applied during each PE step of Frame 6 and Frame 7, such that in corresponding PE steps in Frame 6 and Frame 7, the phase difference between the slice locations S6 and S7 changes by 180° as shown in FIG. 12. A compensating magnetic field gradient may need to be applied in each PE step in Frame 6 and Frame 7 after the readout of the corresponding echo signal and before a next PE step. In some embodiments, the processing device 120 may reconstruct one or more slice images of the slice locations S6 and S7 based on the echo signals acquired in Frame 6 and Frame 7. The reconstruction of the slice image(s) of the slice locations S6 and S7 may be performed in a similar manner with that of the slice image(s) of the slice locations S1 and S2 as described in connection with FIG. 7, and the descriptions thereof are not repeated here.

Figure 13:
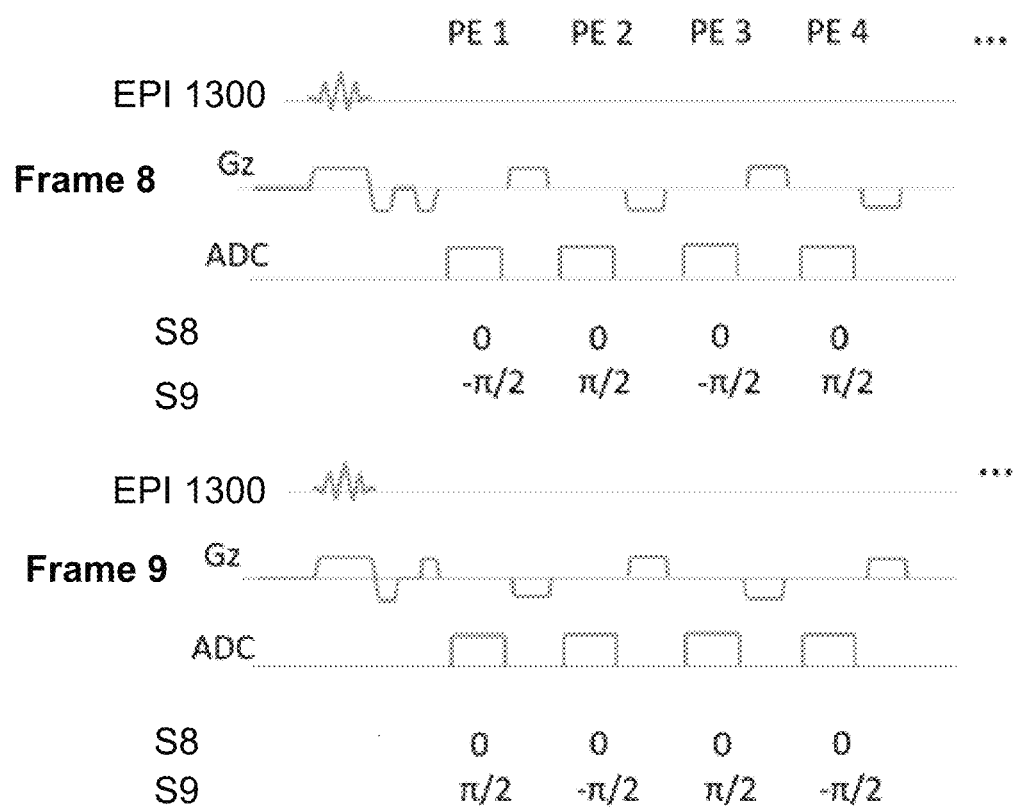
FIG. 13 is a schematic diagram illustrating an exemplary EPI pulse sequence according to some embodiments of the present disclosure.

FIG. 13 is a schematic diagram illustrating an exemplary EPI pulse sequence 1300 according to some embodiments of the present disclosure. The EPI pulse sequence 1300 may be applied by an MR scanner (e.g., the MR scanner 110) to simultaneously imaging a slice location S8 and a slice location S9 of a subject. As shown in FIG. 13, the EPI pulse sequence 1300 may be applied in Frame 8 and Frame 9 with different modulation strategies. During each of the Frames 8 and 9, multiple echoes of different PE steps may be acquired using rephasing gradients after a single RF excitation pulse.

Similar to a bSSFP pulse sequence 700 as described in connection with FIG. 7, a phase modulation gradient may be applied during each PE step in Frame 8 and Frame 9, such that in corresponding PE steps in Frame 8 and Frame 9, the phase difference between the slice locations S8 and S9 changes by 180° as shown in FIG. 13. A compensating magnetic field gradient may need to be applied in each PE step in Frame 8 and Frame 9 after the readout of the corresponding echo signal and before a next PE step. In some embodiments, the processing device 120 may reconstruct one or more slice images of the slice locations S8 and S9 based on the echo signals acquired in Frame 8 and Frame 9. The reconstruction of the slice image(s) of the slice locations S8 and S9 may be performed in a similar manner with that of the slice image(s) of the slice locations S1 and S2 as described in connection with FIG. 7, and the descriptions thereof are not repeated here.

It should be noted that the above exemplary pulse sequences illustrated in FIGS. 7, 11, 12, and 13 and the descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the phase of a certain slice location in a certain PE step may be modulated to any other value which is different from that as shown in figures. In addition, the phase modulation in a certain PE step may be achieved by a phase modulation gradient alone as described above or in combination with a phase modulated RF excitation pulse. Moreover, the Equations provided above are illustrative examples and can be modified in various ways. For example, a plurality of aliasing images of a plurality of frames may be reconstructed, and a reference slice image of a certain slice location may be generated based on any two or more aliasing images of the plurality of aliasing images.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim.

Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for simultaneous multi-slice (SMS) magnetic resonance imaging (MRI), comprising:
    at least one storage device including a set of instructions; and
    at least one processor configured to communicate with the at least one storage device, wherein when executing the set of instructions, the at least one processor is configured to direct the system to perform operations including:
    acquiring a first set of echo signals and a second set of echo signals, the first set of echo signals being acquired by causing an MRI scanner to apply a plurality of first phase-encoding (PE) steps to a first slice location, a second slice location, and a third slice location of a subject in a first frame, the second set of echo signals being acquired by causing the MRI device to apply a plurality of second PE steps to the first slice location, the second slice location, and the third slice location in a second frame, wherein for the PE steps that correspond to PE lines at a same location in K-space and are applied in the first frame and the second frame, a first phase difference between the first slice location and the second slice location of the first frame changes by 120 degrees from a second phase difference between the first slice location and the second slice location of the second frame in one PE step, and a first phase difference between the first slice location and the third slice location of the first frame changes by 240 degrees from a second phase difference between the first slice location and the third slice location of the second frame in one PE step;
    reconstructing a first aliasing image representative of the first slice location, the second slice location, and the third slice location in the first frame based on the first set of echo signals;
    reconstructing a second aliasing image representative of the first slice location, the second slice location, and the third slice location in the second frame based on the second set of echo signals;
    generating, by performing a combination of the first aliasing image and the second aliasing image, a first reference slice image, a second reference slice image, and a third reference image each of which has a lower temporal resolution than the first aliasing image and the second aliasing image the first reference slice image, the second reference image, and the third reference image being respectively representative of the first slice location, the second slice location, and the third slice location in both the first frame and the second frame; and
    reconstructing at least one slice image based on the first aliasing image, the second aliasing image, and at least one of the first reference slice image, the second reference slice image, and the third reference slice image, each slice image of the at least one slice image being representative of one slice location of the first slice location, the second slice location, and the third slice location in one frame of the first frame and the second frame.

2. The system of claim 1, wherein during the first frame and the second frame, the phases of the second slice location and the third slice location in each pair of consecutive PE steps of the plurality of PE steps are different.

3. The system of claim 1, wherein the reconstruction of the at least one slice image based on first aliasing image, the second aliasing image, and the at least one of the first reference slice image, the second reference slice image, and the third reference slice image is performed according to a parallel imaging reconstruction algorithm.

4. The system of claim 1, wherein during at least one PE step in the first frame and the second frame,
    a compensating magnetic field gradient is applied along a slice-encoding direction after a readout of a corresponding echo signal of the first set of echo signals and the second set of echo signals, the compensating magnetic field gradient having a same magnitude as and being in an opposite gradient direction to a phase modulation magnetic field gradient applied in the at least one PE step.

5. The system of claim 1, wherein during at least one PE step in the first frame and the second frame,
    a phase modulated radio frequency (RF) excitation pulse is applied to excite the first slice location, the second slice location, and the third slice location, and a phase modulation in the at least one PE step is achieved by a combination of the phase modulated RF excitation pulse and a phase modulation magnetic field gradient applied in the at least one PE step.

6. The system of claim 1, wherein the plurality of first PE steps and the plurality of second PE steps are applied by at least one of a balanced steady-state free precession (bSSFP) pulse sequence, a fast spin echo (FSE) pulse sequence, an echo planar imaging (EPI) pulse sequence, or a spoiled gradient echo (GRE) pulse sequence.

7. The system of claim 1, wherein during at least one PE step in-the first frame and the second frame, a phase modulation magnetic field gradient is applied along a slice-encoding direction after the first slice location, the second slice location, and the third slice location are excited and before a readout of a corresponding echo signal of the first set of echo signals and the second set of echo signals.

8. The system of claim 1, wherein the operations further include:
acquiring a third set of echo signals by causing the MRI device to apply a plurality of third PE steps to the first slice location, the second slice location, and the third slice location in a third frame, wherein for the PE steps that correspond to PE lines at a same location in K-space and are applied in the first frame and the third frame, the first phase difference between the first slice location and the second slice location of the first frame changes by 240 degrees from a third phase difference between the first slice location and the second slice location of the third frame in one PE step, and the first phase difference between the first slice location and the third slice location of the first frame changes by 480 degrees from a third phase difference between the first slice location and the third slice location of the third frame in one PE step;
reconstructing a third aliasing image representative of the first slice location, the second slice location, and the third slice location in the third frame based on the third set of echo signals;
generating the first reference slice image, the second reference slice image, and the third reference image by performing a combination of the first aliasing image, the second aliasing image, and the third aliasing image; and
reconstructing the at least one slice image based on the first aliasing image, the second aliasing image, the third aliasing image, and at least one of the first reference slice image, the second reference slice image, and the third reference slice image.

9. A method for simultaneous multi-slice (SMS) magnetic resonance imaging (MRI), comprising:
acquiring a first set of echo signals and a second set of echo signals, the first set of echo signals being acquired by causing an MRI scanner to apply a plurality of first phase-encoding (PE) steps to a first slice location, a second slice location, and a third slice location of a subject in a first frame, the second set of echo signals being acquired by causing the MRI device to apply a plurality of second PE steps to the first slice location, the second slice location, and the third slice location in a second frame PE stops, wherein for the PE steps that correspond to PE lines at a same location in K-space and are applied in the first frame and the second frame, a first phase difference between the first slice location and the second slice location of the first frame changes by 120 degrees from a second phase difference between the first slice location and the second slice location of the second frame in one PE step, and a first phase difference between the first slice location and the third slice location of the first frame changes by 240 degrees from a second phase difference between the first slice location and the third slice location of the second frame in one PE step;
reconstructing a first aliasing image representative of the first slice location, the second slice location, and the third slice location in the first frame based on the first set of echo signals;
reconstructing a second aliasing image representative of the first slice location, the second slice location, and the third slice location in the second frame based on the second set of echo signals;
generating, by performing a combination of the first aliasing image and the second aliasing image, a first reference slice-image, a second reference slice image, and a third reference image each of which has a lower temporal resolution than the first aliasing image and the second aliasing image the first reference slice image, the second reference image, and the third reference image-being respectively representative of the first slice location, the second slice location, and the third slice location in both the first frame and the second frame; and
reconstructing at least one slice image based on the first aliasing image, the second aliasing image, and at least one of the first reference slice image, the second reference slice image, and the third reference slice image, each slice image of the at least one slice image being representative of one slice location of the first slice location, the second slice location, and the third slice location in one frame of the first frame and the second frame.

10. The method of claim 9, wherein during the first frame and the second frame, the phases of the second slice location and the third slice location in each pair of consecutive PE steps of the plurality of PE steps are different.

11. The method of claim 9, wherein the reconstruction of the at least one slice image based on the first aliasing image, the second aliasing image, and the at least one of the first reference slice image, the second reference slice image, and the third reference slice image is performed according to a parallel imaging reconstruction algorithm.

12. The method of claim 9, wherein during at least one PE step in the first frame and the second frame,
a compensating magnetic field gradient is applied along a slice-encoding direction after a readout of a corresponding echo signal of the the first set of echo signals and the second set of echo signals, the compensating magnetic field gradient having a same magnitude as and being in an opposite gradient direction to a phase modulation magnetic field gradient applied in the at least one PE step.

13. The method of claim 9, wherein during at least one PE step in the first frame and the second frame,
a phase modulated radio frequency (RF) excitation pulse is applied to excite the the first slice location, the second slice location, and the third slice location, and a phase modulation in the at least one PE step is achieved by a combination of the phase modulated RF excitation pulse and a phase modulation magnetic field gradient applied in the at least one PE step.

14. The method of claim 9, wherein the plurality of first PE steps and the plurality of second PE steps are applied by at least one of a balanced steady-state free precession (bSSFP) pulse sequence, a fast spin echo (FSE) pulse sequence, an echo planar imaging (EPI) pulse sequence, or a spoiled gradient echo (GRE) pulse sequence.

15. The method of claim 9, wherein during at least one PE step in the first frame and the second frame, a phase modulation magnetic field gradient is applied along a slice-encoding direction after the first slice location, the second slice location, and the third slice location are excited and before a readout of a corresponding echo signal of the first set of echo signals and the second set of echo signals.

16. The method of claim 9, wherein the method further includes:
acquiring a third set of echo signals by causing the MRI device to apply a plurality of third PE steps to the first slice location, the second slice location, and the third slice location in a third frame, wherein for the PE steps that correspond to PE lines at a same location in K-space and are applied in the first frame and the third frame, the first phase difference between the first slice location and the second slice location of the first frame changes by 240 degrees from a third phase difference between the first slice location and the second slice location of the third frame in one PE step, and the first phase difference between the first slice location and the third slice location of the first frame changes by 480 degrees from a third phase difference between the first slice location and the third slice location of the third frame in one PE step;
reconstructing a third aliasing image representative of the first slice location, the second slice location, and the third slice location in the third frame based on the third set of echo signals;
generating the first reference slice image, the second reference slice image, and the third reference image by performing a combination of the first aliasing image, the second aliasing image, and the third aliasing image; and
reconstructing the at least one slice image based on the first aliasing image, the second aliasing image, the third aliasing image, and at least one of the first reference slice image, the second reference slice image, and the third reference slice image.

17. A non-transitory computer-readable storage medium including instructions for simultaneous multi-slice (SMS) magnetic resonance imaging (MRI), that, when accessed by at least one processor of a system, causes the system to perform a method, the method comprising:
acquiring a first set of echo signals and a second set of echo signals, the first set of echo signals being acquired by causing an MRI scanner to apply a plurality of first phase-encoding (PE) steps to a first slice location, a second slice location, and a third slice location of a subject in a first frame, the second set of echo signals being acquired by causing the MRI device to apply a plurality of second PE steps to the first slice location, the second slice location, and the third slice location in a second frame, wherein for the PE steps that correspond to PE lines at a same location in K-space and are applied in the first frame and the second frame, a first phase difference between the first slice location and the second slice location of the first frame changes by 120 degrees from a second phase difference between the first slice location and the second slice location of the second frame in one PE step, and a first phase difference between the first slice location and the third slice location of the first frame changes by 240 degrees from a second phase difference between the first slice location and the third slice location of the second frame in one PE step;
reconstructing a first aliasing image representative of the first slice location, the second slice location, and the third slice location in the first frame based on the first set of echo signals;
reconstructing a second aliasing image representative of the first slice location, the second slice location, and the third slice location in the second frame based on the second set of echo signals;
generating, by performing a combination of the first aliasing image and the second aliasing image, a first reference slice image, a second reference slice image, and a third reference image each of which has a lower temporal resolution than the first aliasing image and the second aliasing image, the first reference slice image, the second reference image, and the third reference image being respectively representative of the first slice location, the second slice location, and the third slice location in both the first frame and the second frame; and
reconstructing at least one slice image based on the first aliasing image, the second aliasing image, and at least one of the first reference slice image, the second reference slice image, and the third reference slice image, each slice image of the at least one slice image being representative of one slice location of the first slice location, the second slice location, and the third slice location in one frame of the first frame and the second frame.

* * * * *